United States Patent [19]
Flynn

[11] Patent Number: 5,054,310
[45] Date of Patent: * Oct. 8, 1991

[54] TEST OBJECT AND METHOD OF MEASUREMENT OF AN ULTRASONIC BEAM

[75] Inventor: John J. Flynn, Los Angeles, Calif.

[73] Assignee: The California Province of the Society of Jesus, Los Gatos, Calif.

[*] Notice: The portion of the term of this patent subsequent to Feb. 27, 2007 has been disclaimed.

[21] Appl. No.: 439,081

[22] Filed: Nov. 20, 1989

Related U.S. Application Data

[63] Continuation-in-part of Ser. No. 97,579, Sep. 16, 1987, Pat. No. 4,903,523, which is a continuation-in-part of Ser. No. 775,754, Sep. 13, 1985, abandoned.

[51] Int. Cl.⁵ .............................................. G09B 23/14
[52] U.S. Cl. ................................................... 73/1 DV
[58] Field of Search .................. 73/1 DV, 1 R, 866.4; 128/660.01, 916; 367/13

[56] References Cited

U.S. PATENT DOCUMENTS

| | | | |
|---|---|---|---|
| 4,331,021 | 5/1982 | Lopez et al. ...................... | 73/1 DV |
| 4,417,582 | 11/1983 | Trimmer et al. ............. | 73/1 DV X |
| 4,453,408 | 6/1984 | Claymen .......................... | 73/1 DV |
| 4,493,653 | 1/1985 | Robbins et al. ................. | 73/866.4 X |
| 4,567,896 | 2/1986 | Barnea et al. ..................... | 73/1 R X |
| 4,704,892 | 11/1987 | Tarnai ............................... | 73/1 DV |
| 4,729,235 | 3/1988 | Podlech ............................ | 73/1 DV |
| 4,923,155 | 5/1990 | Dainis et al. ..................... | 73/1 R X |

Primary Examiner—Noland, Tom
Attorney, Agent, or Firm—Lyon & Lyon

[57] ABSTRACT

A test object for use in determining the accuracy of and to calibrate ultrasonic scanning equipment is disclosed. The test object provides for the determination of elevational resolution. Additionally, the test object provides for the determination of the existence, location, intensity and width of side lobes, both substantially in the direction of the scanning plane and in substantially the direction normal to the scanning plane.

12 Claims, 8 Drawing Sheets fig. 1.

TEST OBJECT AND METHOD OF MEASUREMENT OF AN ULTRASONIC BEAM

RELATED APPLICATIONS

This application is a continuation in part of application Ser. No. 097,599, filed Sept. 16, 1987, and now U.S. Pat. No. 4,903,523 which is itself a continuation in part of application Ser. No. 775,754 filed Sept. 13, 1985 and now abandoned.

BACKGROUND OF THE INVENTION

1. Field of the Invention

The present invention relates generally to medical diagnosis and more particularly to the non-destructive testing and non-invasive examination of soft-tissue and body organs using ultrasonic diagnostic equipment. Specifically this invention is directed to a test object used to test the accuracy of and calibrate ultrasonic diagnostic equipment, such as pulse echo body scanners and the like, presently used by many hospitals and doctors.

2. Description of the Prior Art

Apparatus and techniques which permit the nondestructive testing and non-invasive examination of soft tissue and body organs are of particular interest to the medical community. Examples of presently available techniques include x-ray, nuclear medicine, thermography and diagnostic ultrasound. Ultrasonic diagnostic techniques are important because they offer a very high benefit to risk ratio for the patient and the ability to perform quality imaging of soft tissue organs. Thus ultrasonic diagnosis has found widespread applicability to the medical subfields of obstetrics, gynecology, cardiology, neurology, ophthalmology and urology among others. Ultrasonic diagnostic has proved of particular value as a diagnostic aid for the pregnant uterus including fetus and placenta, eye, breast, brain, lung, kidney, liver, gall bladder, bile ducts, pancreas, spleen, heart and blood vessels and soft tissues of extremities of neck including thyroid and parathyroid glands.

Ultrasonic diagnostic instruments operate on either a pulse-echo or Doppler principle. These principles are both well known. Most frequently the imaging of soft body tissue is accomplished using the pulse-echo principle. Short bursts of ultrasonic energy are transmitted into the body and the echoes are recorded. The time required for an emitted pulse to return as an echo provides an indication of the distance of a measured structure. Echoes occur at the boundaries between different tissues within the body since a fraction of the incident energy is deflected whenever the characteristic impedance of the structure under examination changes. Typically a change in the characteristic impedance occurs at such a boundary. Impedance is defined as the product of the density of the tissue multiplied by the velocity of sound. The first boundary will not typically reflect all the incident energy which may be reflected at subsequent boundaries. Thus, various boundaries at various depths can be observed.

Ultrasonic diagnostic equipment is used by a process called scanning. Scanning involves the movement of a pulsed sound beam propagated by a transducer through a plane. The transducer converts electrical signals into acoustic pulses. Through scanning a two-dimensional image of the various organs or body regions of interest are generated.

The quality of the two-dimensional image generated through the scanning process is dependent on the axial, lateral and elevational resolution of the transmitted ultrasonic beam and the absence or presence of side lobes. Resolution is also substantially dependent on the cross-section of the ultrasonic beam at various depths.

A known method of measuring the resolution of an ultrasonic beam employs measurement of the intensity of an ultrasonic beam using a hydrophone in an open tank of water at various depths in an engineering laboratory setting. This is impractical and not available in most clinical laboratories. For this reason, simple test objects have been devised in recent years to measure beam parameters.

A method and device for determining the axial and lateral resolution of the ultrasonic beam and the beam width in the direction of the scanning plan was adopted by the American Institute of Ultrasound in Medicine (AIUM) in 1974. The device involves the use of scanning targets immersed in an air-free scanning medium whose velocity of sound substantially corresponds to that of the soft body tissue being examined. Typically, the velocity of sound in human tissue is 1540 m/s. The construction and use of this device is fully described in chapters 7 and 9.2 of a Department of Health and Human Services publication, FDA 818139, in its Bureau of Radiological Health Quality Assurance Series entitled "Quality Assurance in Diagnostic Ultrasound Manual for the Clinical User" authored by Albert Goldstein, Ph.D. and published in October, 1980. This document in its entirety is incorporated herein by reference.

Trimmer (U.S. Pat. No. 4,417,582) provides a device and method for measuring lateral resolution in the scanning plane which differ from the AIUM test object in that it allows for continuous measurements of lateral resolution rather than the discrete measurements that characterize the AIUM test object. Clayman (U.S. Pat. No. 4,453,408) describes a device that produces a profile of the beam, thus providing for a continuous range of beam width measurements.

All of devices above are inadequate for determining the width of the ultrasonic beam in a direction substantially normal to the scanning plane, sometimes referred to as "out-of-plane beam width" or "elevational resolution" or "slice thickness," an important measurement when the ultrasonic diagnostic equipment being used generates a noncircular beam cross-section. Additionally these devices do not provide for a method to determine the existence, location, width or intensity of side lobes in either substantially the direction of the scanning plane or in the direction substantially normal to the scanning plane.

SUMMARY OF THE INVENTION

Accordingly, it is the purpose of the present invention to provide a test object comprising an arrangement of scanning targets that provide for the determination of the ultrasonic beam width in the direction substantially normal to the scanning plane and the existence of side lobes both in substantially the direction of the scanning plane and in the direction substantially normal to the scanning plane in addition to the axial and lateral resolution of the ultrasonic beam and the beam width in the direction of the scanning plane.

DESCRIPTION OF THE PREFERRED EMBODIMENTS

Figure 1:
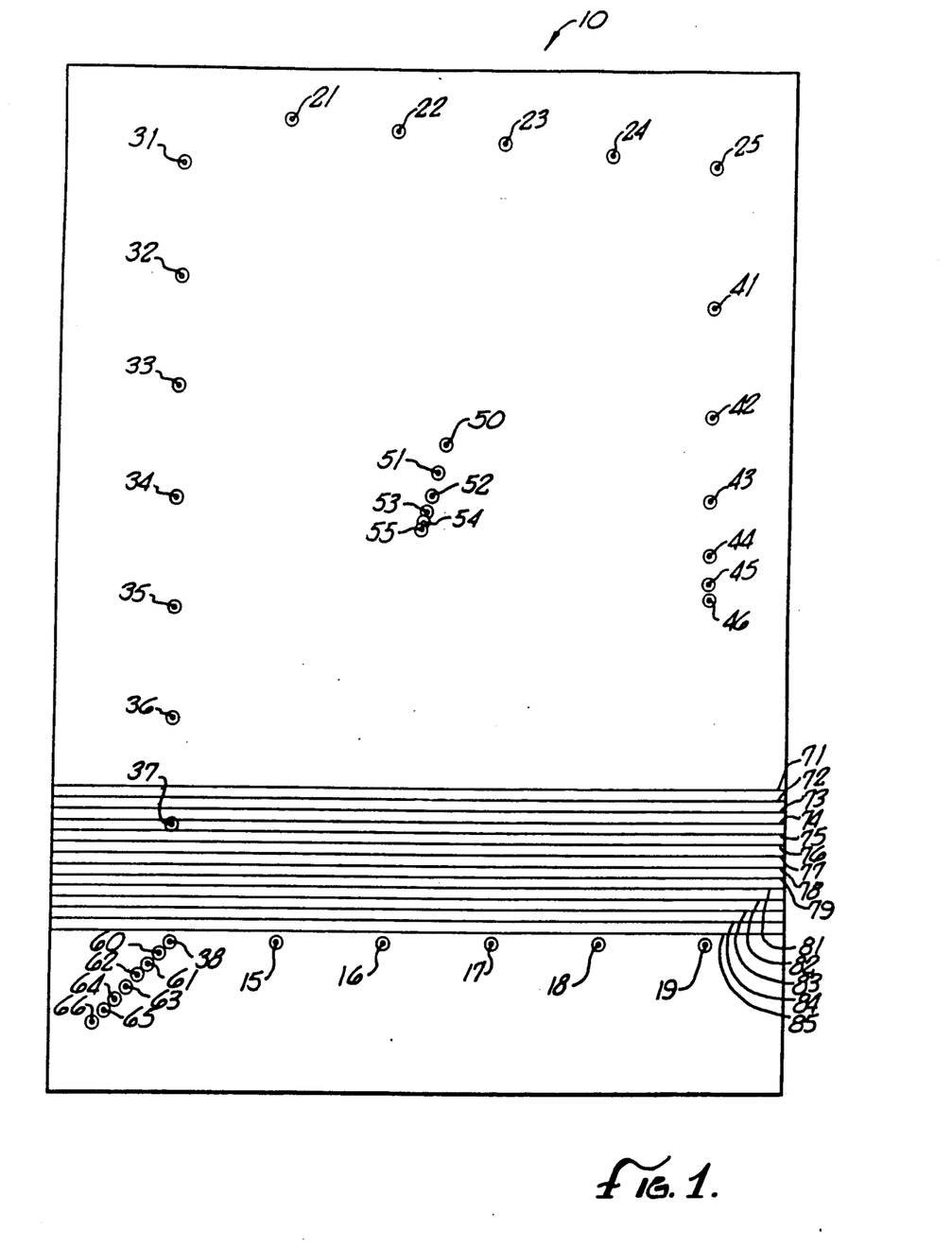
FIG. 1 is a side view, perpendicular to the scanning plane, of the AIUM test object modified in accordance with one aspect of the present invention.

Referring to FIG. 1, a modified AIUM test object (10) is shown suitable for the determination of the axial and lateral resolution of the ultrasonic beam and the beam width in the direction of the scanning plane and in the direction substantially normal to the scanning plane. Additionally the test object is suitable for the determination of the existence, location, intensity or width of side lobes in substantially the direction of the scanning plane and in the direction substantially normal to the scanning plane. The size of the test object shown is for illustration only. The test object can be larger or smaller as required.

For reference purposes (still referring to FIG. 1), the axial direction or depth of the beam is from top to bottom, the lateral direction or in-plane width extends normal to the plane of the figure. Down-range means toward the bottom of the test object, away from the transducer. Up-range means toward the top of the test object and the transducer.

An ultrasonic beam, not shown, is moved back and forth through the test object (10) in the direction of the scanning plane. A portion of the beam will be reflected if it intersects a scanning target thereby forming an echo that will be recorded by undepicted ultrasonic diagnostic equipment.

The scanning targets are generally rods or wires of stainless steel or nylon filaments or the like and should have a minimum cross-sectional area sufficient to create a measurable echo. Cylindrical rods having a 0.75 mm cross-section are satisfactory. The scanning targets are supported by affixing each end of the rod in an end plate of acrylic plastic or the like.

In use the test object (10) is generally immersed in an air-free medium whose velocity of sound corresponds to that of the tissues being examined. Water is a satisfactory medium and when used at a temperature of 47° C. closely corresponds to the average velocity of sound in tissue of 1540 m/s. Other mediums and their use are commercially available and are known in the art.

Scanning targets (15, 16, 17, 18, 19 and 38) are used for horizontal calibration and measurement of horizontal linearity. Scanning targets (21, 22, 23, 24 and 25) are used in the determination of the dead zone or ring down distance for the equipment being used. Scanning targets (31, 32, 33, 34, 35, 36, 37 and 38) are used for depth calibration and beam width in the direction of the scanning plane. Scanning targets (25, 41, 42, 43, 44, 45 and 46) are used to determine the lateral resolution of the ultrasonic beam in the direction of the scanning plane. Scanning targets (50, 51, 52, 53, 54 and 55) are used in the determination of axial resolution. The number of targets depicted is for illustration only; more or less targets can be used as required. The use of these scanning targets is known in the art. A detailed explanation of their use can be found in the AIUM publication previously referred to and which is incorporated herein by reference.

However it has not been known how to determine the width of the ultrasonic beam in a direction substantially orthogonal to the scanning plane nor how to determine the existence, location or intensity of side lobes in substantially the direction of the scanning plane or in the direction substantially normal to the scanning plane by means of a simple test object.

Scanning targets (60, 61, 62, 63, 64, 65 and 66) are used in the determination of the existence, location, intensity and width of side lobes substantially in the direction of the scanning plane. When the depth calibration of the transducer is being performed using scanning targets (31, 32, 33, 34, 35, 36, 37 and 38) the presence or absence, and characteristics if present, of a side lobe is determinable by using these scanning targets (60, 61, 62, 63, 64, 65 and 66).

The location for scanning targets (60, 61, 62, 63, 64, 65 and 66) is dependent on the ultrasonic diagnostic equipment being used. As a group, the targets should be positioned approximately where the location of a side lobe is predicted by well-known physical principles. From each other, the lateral spacing of the targets is preferably small, within construction limitations, for greater precision. The targets are axially displaced to allow for axial discrimination. The axial displacement of the targets is preferably as small as possible, but generally no smaller than the axial resolution of the equipment being used. Displacing the targets by 2 mm in the axial direction and 2 mm in the lateral directions is generally satisfactory for 1–3.5 megahertz equipment. For higher frequency equipment less spacing between the targets is generally required. This invention is not limited, in any way, to the number of targets shown. More or less targets can be used. More targets are likely to be used if it is necessary to determine the presence of second order or other higher orders of side lobes. Additionally, the targets can be moved up or down in the test object as required.

Figure 2:
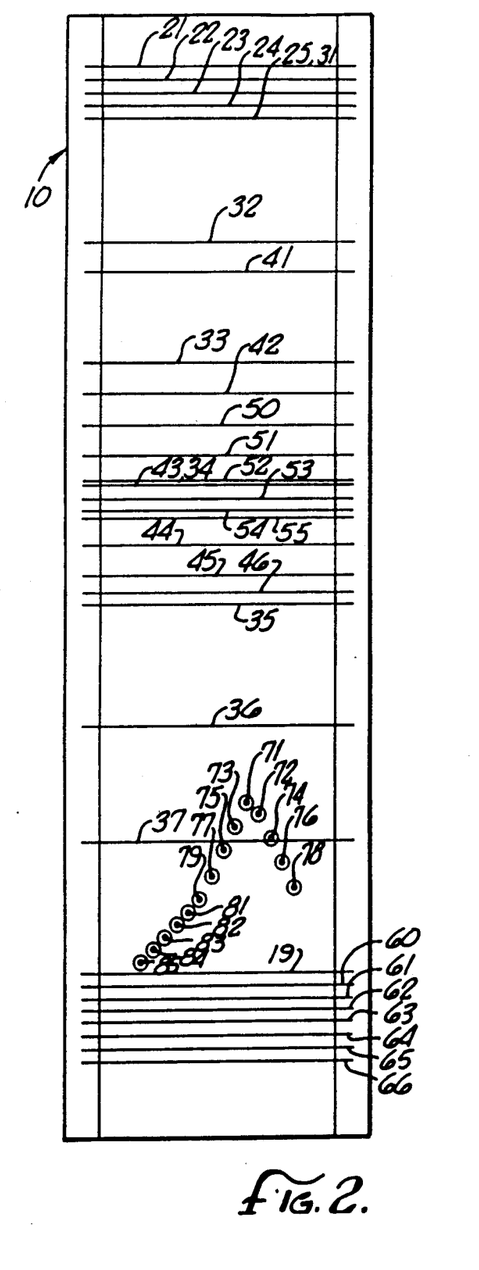
FIG. 2 is an end view of the test object depicted in FIG. 1.

Referring to FIG. 2, scanning targets (71, 72, 73, 74, 75, 76, 77, 78 and 79) are used in the determination of the width of the ultrasonic beam in a direction substantially normal to the scanning plane. As the ultrasonic beam is moved back and forth in the scanning plane centered to be coincident with the apices of the scanning targets some of the targets will produce an echo. The number of wires detected and echoes recorded will indicate the width of the scanning beam in the direction substantially normal to the scanning plane. The targets are axially displaced to provide for the counting of the number of targets that are intersected by the ultrasonic beam. The axial displacement of the targets is preferably as small as possible, but generally no smaller than the axial resolution of the equipment being used. Displacing the targets by 2 mm in the axial direction and 2 mm in the lateral direction from each other target is generally satisfactory for 1–3.5 megahertz equipment. As previously stated, less spacing between targets is preferred when higher frequency equipment is used. If 2 mm axial and lateral displacement is used, target (75) is laterally displaced by 2 mm from targets (73) and (77) and axially displaced by 4 mm from targets (73) and (77) since target (75) is axially displaced by 2 mm from targets (74) and (76). Again, the invention is not limited by the number of targets shown. As a group the targets can be moved up, down, front or back as required.

Scanning targets (81, 82, 83, 84 and 85) are used in determining the existence, location, intensity and width of side lobes substantially normal to the scanning plane. This determination occurs when the width of the ultrasonic beam is determined in a direction substantially normal to the scanning plane by moving the ultrasonic beam back and forth in the scanning plane centered above the cluster of scanning targets (71, 72, 73, 74, 75, 76, 77, 78 and 79). As a group, the targets (81, 82, 83, 84 or 85) should be positioned approximately where the location of a side lobe is predicted. From each other, the axial and lateral spacing of these targets will be similar to the axial and lateral spacing of targets (60, 61, 62, 63, 64, 65 and 66). Again, the number of targets is not limited, in any way, to the number of targets shown. Also, the targets can be moved up or down in the test object as required.

Figure 3:
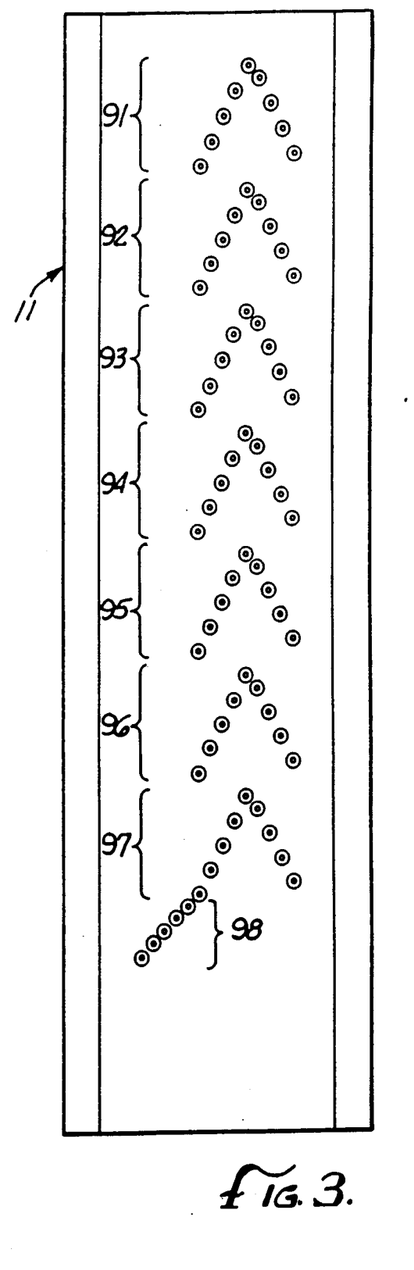
FIG. 3 is an end view of an alternative test object constructed in accordance with another aspect of the present invention.

Referring to FIG. 3, clusters of scanning targets are shown in test object (11) to determine the width of the ultrasonic beam in a direction substantially normal to the scanning plane at various depths. Within each cluster the targets are used and positioned as previously described. While other configurations are possible using more or less clusters, more or less scanning targets in each cluster, or clusters at different distances from the transducer, the figure depicts nine scanning targets in each cluster. The top cluster (91) has scanning targets at varying distances from the transducer, not shown, from one to three centimeters. The targets of cluster (92) vary from three to five centimeters from the transducer. The same pattern of spacing is used for the targets of clusters (93, 94, 95, 96 and 97). The clusters can continue, as required, until the maximum usable depth of the transducer is obtained, currently about 20 cms. Also shown are the targets of cluster (98) used in the determination of the existence, location, intensity and width of side lobes in the direction substantially normal to the scanning plane as previously described. Cluster (98) need not be placed at the bottom of the test object. As required more scanning targets can be added to test object (11) for the determination of the characteristics of the ultrasonic beam.

Figure 4:
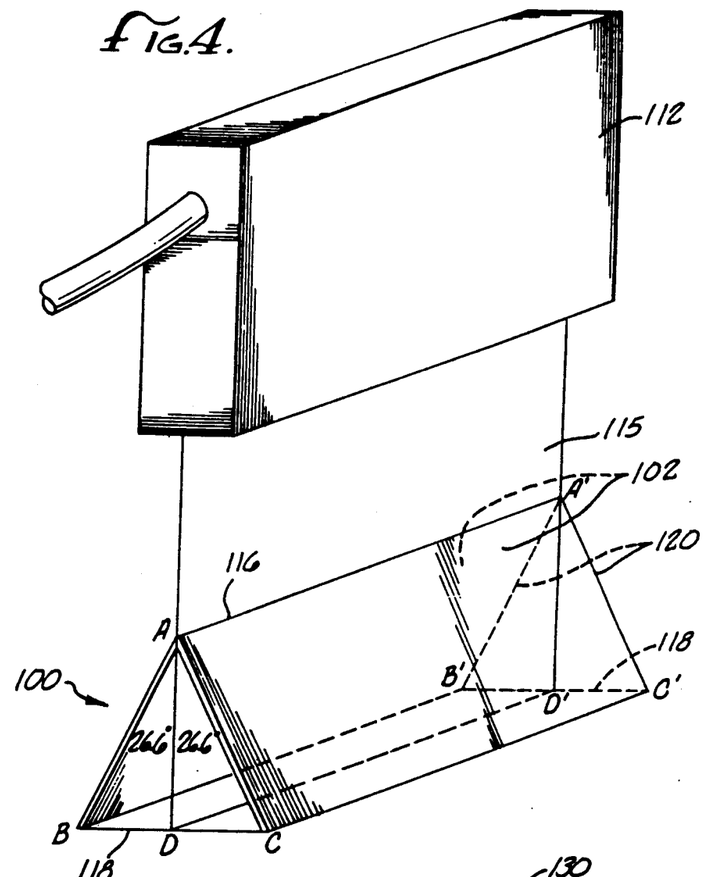
FIG. 4 is a perspective view of a single cluster of targets providing a continuous measurement of the slice thickness of the beam within a specific range.

FIG. 4 shows a wedge-shaped cluster of targets (100) similar to the wedge-shaped clusters of FIGS. 2 and 3 wherein the targets are formed by a cloth fabric made of nylon or other echogenic material having a suitable acoustic impedance mismatch with reference to the transmitting medium. The fabric is affixed to a wedge-shaped plastic support structure (102). The threads of the nylon cloth mesh are about 0.5 mm apart. Alternatively a wedged-shaped cluster of targets can be formed by coating the support structure (102) with echogenic particles such as graphite or the like having suitable acoustic impedance mismatch with reference to the transmitting medium. Positioned above the targets is a transducer assembly (112) aligned such that the scan plane (115) intersects the apex (116) and bisects the base (118) of the target wedge (100). Targets forming the apex of the wedge (100) will reflect the in-plane component of the beam, and these echoes will generate a well defined specular image representing the theoretical scan plane. Targets forming the sides (120) of the target wedge (100) will reflect the out-of-plane component of the beam at a plurality of ranges, and will generate a diffuse band image whose height is proportional to the out-of-plane beam width at the range of the outermost reflecting targets. Preferably, the sides (120) of the wedge (100) diverge from the scan plane at equal and opposite angles of 26.6 degrees so that the base is equal to the height of the wedge. When the beam intersects the targets, an image is produced whose vertical height is equal to the width of the beam perpendicular to the scan plane.

Figure 5:
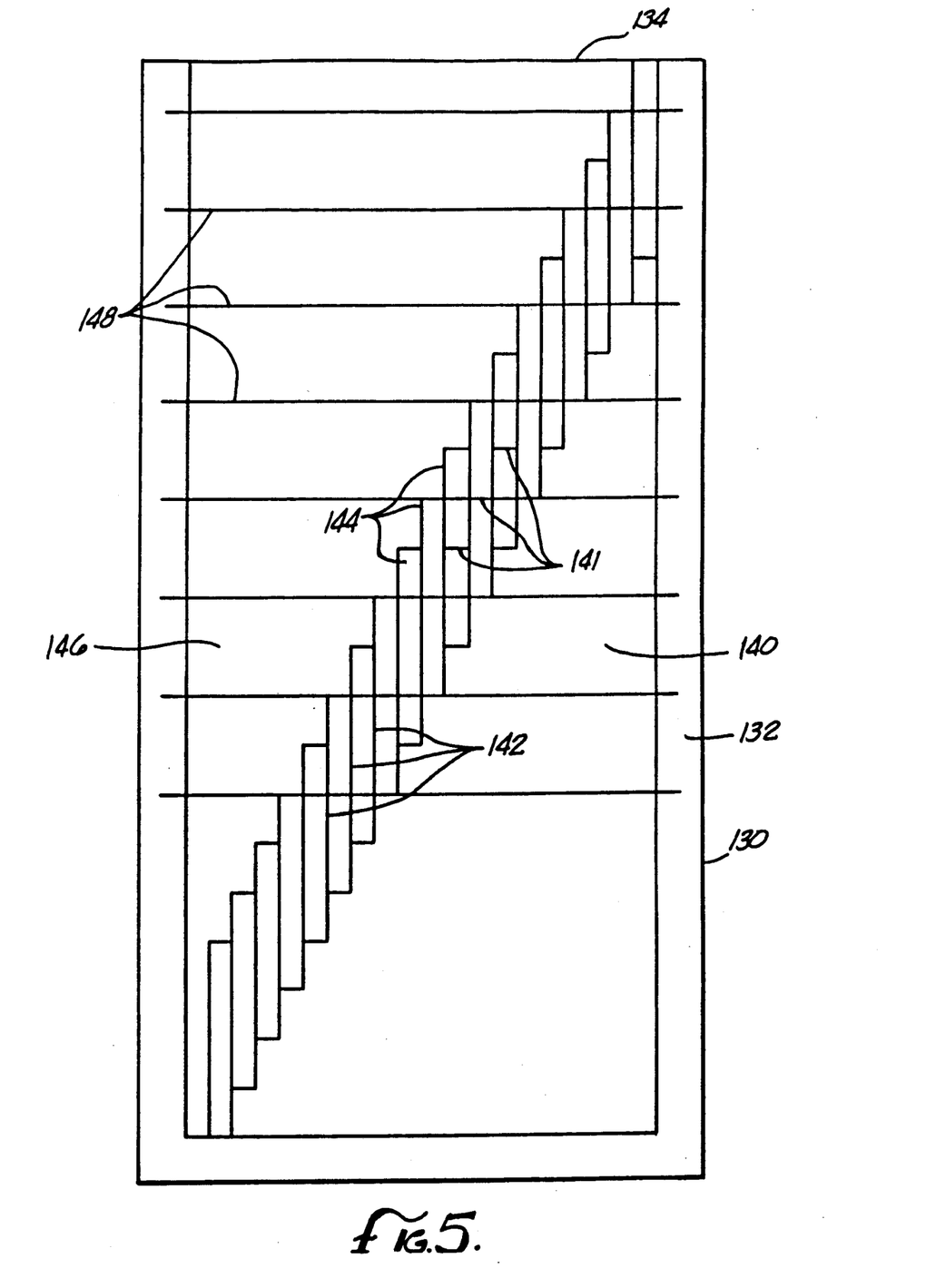
FIG. 5 is a side view of a test object constructed in accordance with yet another aspect of the present invention looking perpendicular to the scanning plane showing multiple clusters of targets mounted on the steps of a step wedge platform.
Figure 6:
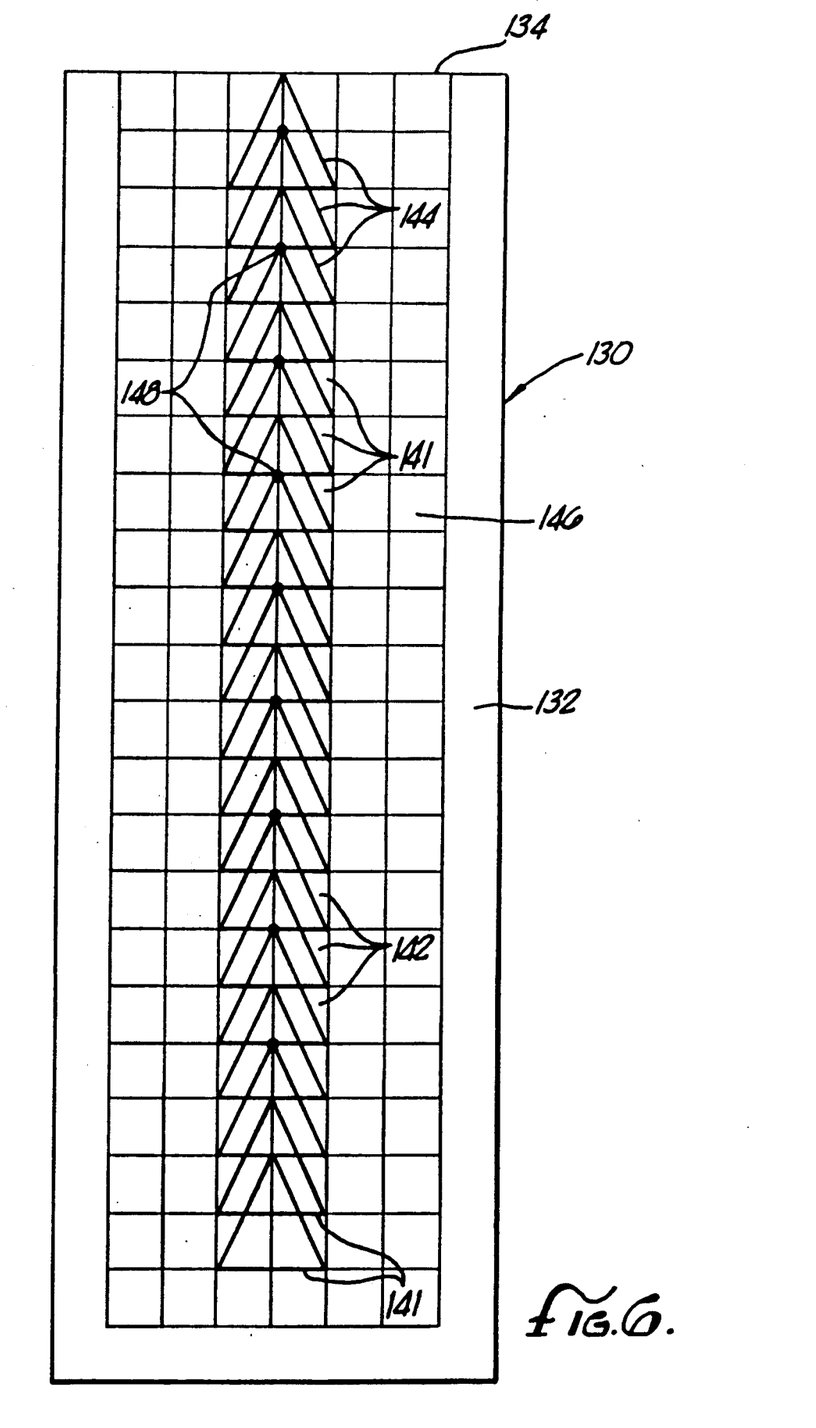
FIG. 6 is an end view of the object depicted in FIG. 5.
Figure 7:
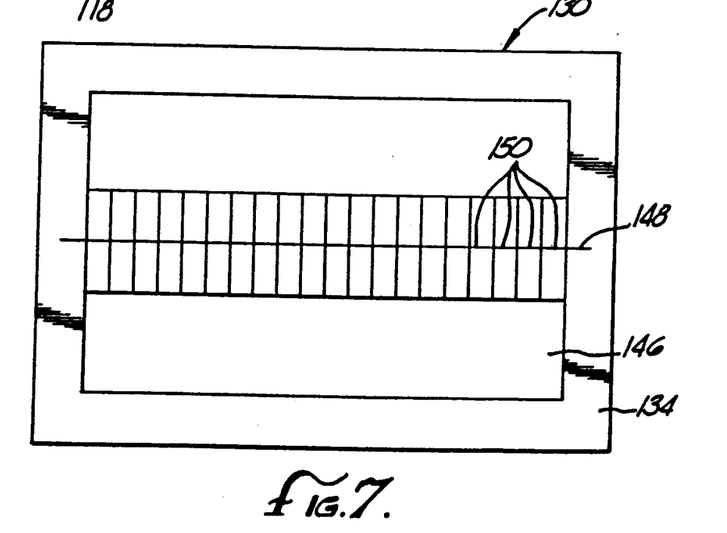
FIG. 7 is a top view of the object depicted in FIG. 5.

FIG. 5 depicts an arrangement whereby a detailed description of the out-of-plane beam shape may be obtained by placing wedge-shaped clusters of targets at appropriate ranges with the apices of the wedges aligned in the scan plane. A test object (130) comprises a frame (132) having a top (134), above which is positioned a transducer (not shown) generating a scan plane (not shown) parallel to the plane of the figure. Provided within the test object (130) is a step wedge platform (140) comprising a series of steps (141) and risers (142) upon which are mounted a plurality of wedge-shaped clusters of targets (144). Preferably the clusters (144) diverge from the scan plane in an amount sufficient to detect at least the first side lobe in a direction substantially normal to the scan plane. The test object (130) is filled with a tissue equivalent medium (146). Also positioned within the test object (130) are a series of ultrasonic guide wires (148) that are coincidental with the scan plane and positioned at depths of 1, 3, 5, 7, 9, 11, 13 and 15 cm respectively. The guide wires (148) are used for aligning the scan plane with the apices (150) of the wedges (144).

Figure 8:
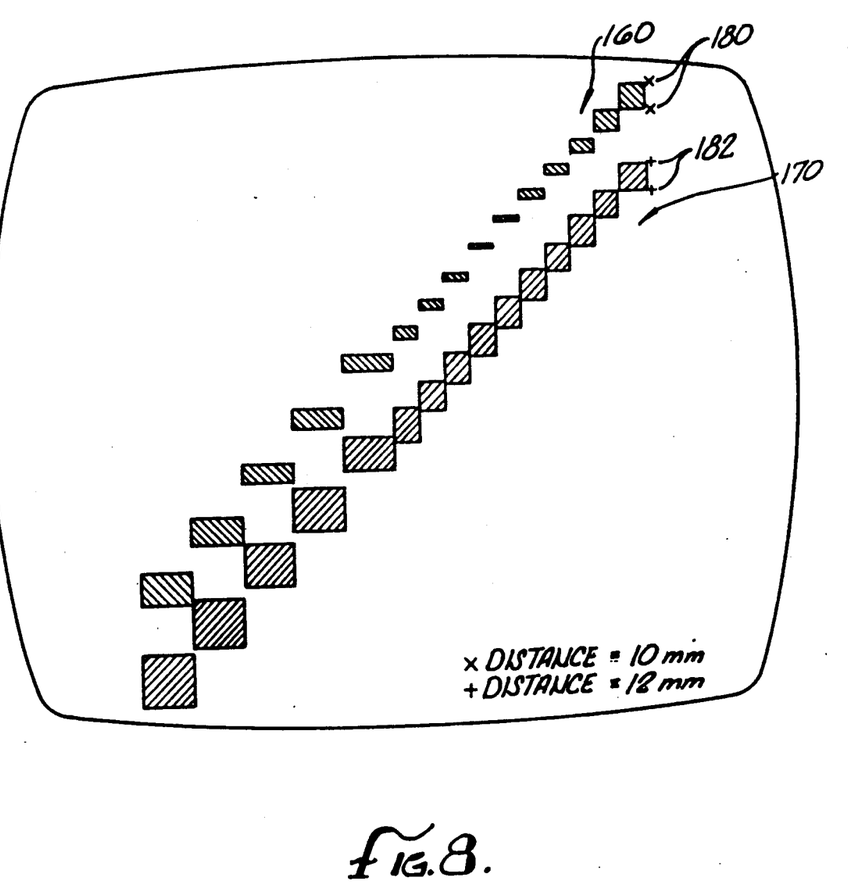
FIG. 8 is a front view of an image monitor showing a pair of electronic calipers (x,x) measuring the slice thickness of the beam at the level of the top target element and a second pair of electronic calipers (+,+) measuring the width of the first side lobe in the direction substantially normal to the scanning plane.

FIG. 8 depicts a typical scan obtained from the test object (130). The upper diagonal row of squares (160) represents the actual beam width as a function of depth. The lower diagonal row of squares (170) represents side lobes associated with the beam. A pair of electronic calipers (180) are shown measuring the out-of-plane beam width of the beam at the level of the top cluster of targets and a second pair of electronic calipers (182) are shown measuring the width of the first side lobe in the direction substantially normal to the scan plane.

Figure 9:
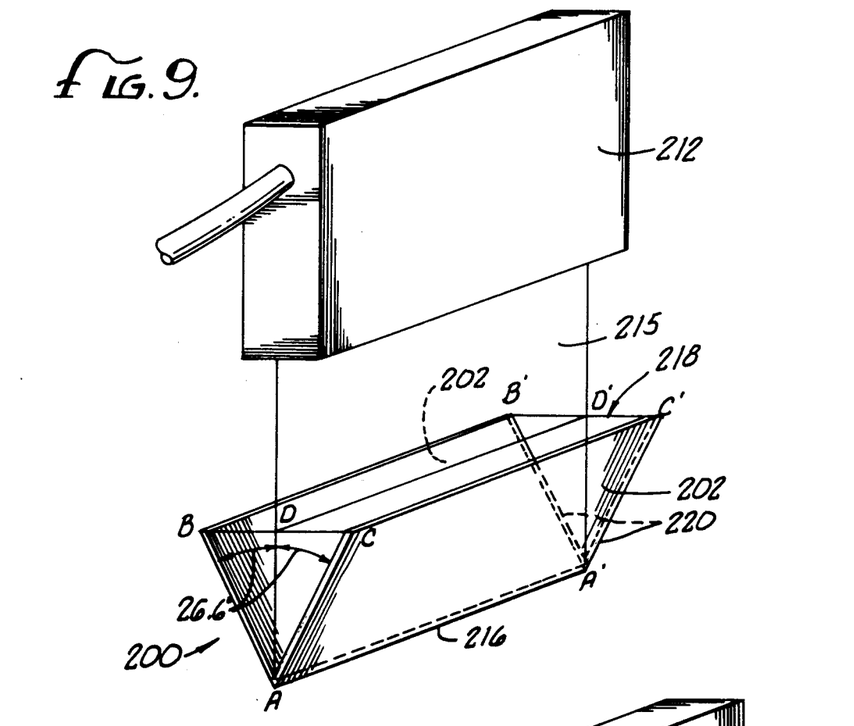
FIG. 9 is a perspective view of an alternative test object constructed in accordance with a further aspect of the present invention.

FIG. 9 shows an alternative embodiment of a target wedge (200) similar to that shown in FIG. 4 except that the wedge (200) is inverted so that the imaginary base (218) is up and the vertex (216) is down. The target clusters (202), similar to those described in FIG. 4 (102), are affixed to the inside of each side (220) of the wedge (200) opposite the imaginary base (218) instead of to the outsides of the sides (120) of the wedge (100) as seen in FIG. 4. Thus the wedge (200) comprises at least one scanning target positioned in the scanning plane occupying a terminal position, i.e., the vertex of the wedge, and a plurality of subsequent scanning targets positioned adjacent the scanning plane, i.e., the sides of the wedge, extending up-range from the terminal target(s).

The scanning plane of the ultrasound beam (215) transmitted from the transducer assembly (212) is positioned so as to bisect the imaginary base (218) of the wedge (200) along the line D D' and to coincide with its vertex (216) along lines A A' so as to form an angle of 26.6 degrees between the scanning plane (215) and the sides (220) of the wedge (200). As in the case of the wedge (100) in FIG. 4, the targets may be the mesh of a cloth fabric or echogenic particles such as graphite (wire targets could also be used). This layer of target material (202) is affixed to the insides of the sides (220) of the wedge-shaped support structure (200) made of plastic or other solid material having a planar surface. The sides (220) thus form a substrate upon which the targets are mounted. Targets (202) affixed to the sides (220) of the target wedge (200) will reflect the out-of-plane beam at a plurality of ranges (all up-range from the vertex), and these echoes will generate a diffuse band image whose height is equal to the out-of-plane beam width at the range of the outermost insonated reflecting targets. When the beam thus interacts with the targets, an image is produced whose vertical height is equal to the width of the beam orthogonal to the scanning plane.

Figure 10:
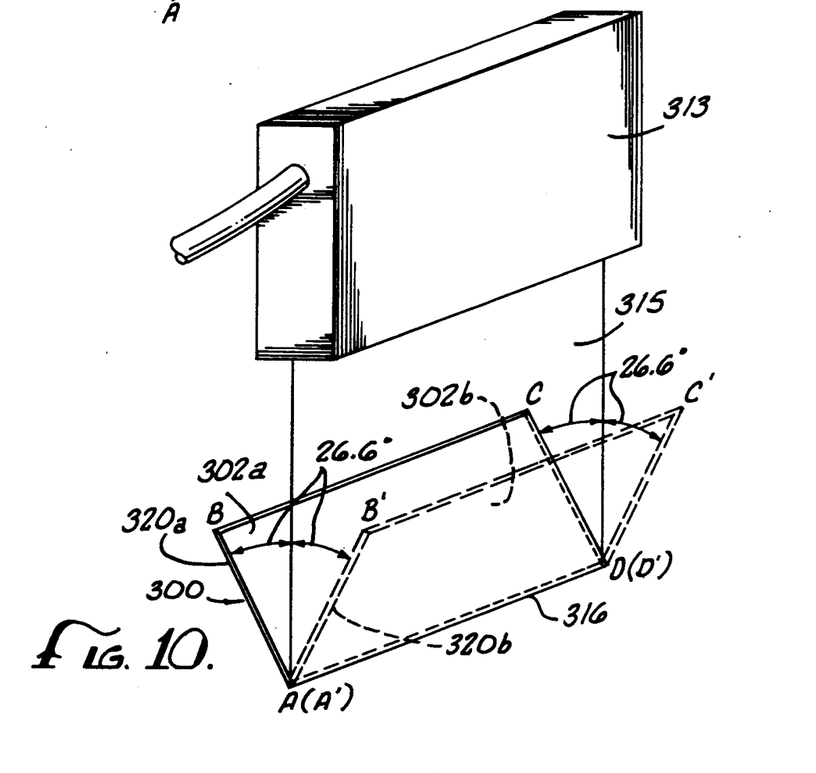
FIG. 10 is a perspective view of another alternative test object constructed in accordance with a still further aspect of the present invention.

An alternate single sided embodiment is shown in FIG. 10. A single reflective plane (300a) consists of a layer of reflective target clusters (302a) such as the mesh of a cloth fabric or echogenic particles such as graphite as described above for the wedge targets (wire targets could also be used). The layer of reflective targets is affixed to a planar support structure (320a) made of plastic or other solid material which thus forms a substrate. The reflective plane (302a) can be tilted to one side of the scanning plane as reflective plane ABCD or to the other side of the scanning plane as reflective plane A'B'C'D' (300b), comprising a layer of reflective target clusters (302b) affixed to a planar support structure (320b). The lower edge 316 of the reflective plane (300a) is aligned along AD with the scanning plane 315. The reflective plane (300a) thus comprises at least one target positioned in the scanning plane occupying a terminal position and a plurality of subsequent scanning targets positioned adjacent the scanning plane. The angle of tilt of the reflective plane is 26.6 degrees from the scanning plane, and the reflective surface (302a) is on the beam side of the planar support structure (320a). The subsequent scanning targets are positioned up-range from the terminal target(s).

Figure 11:
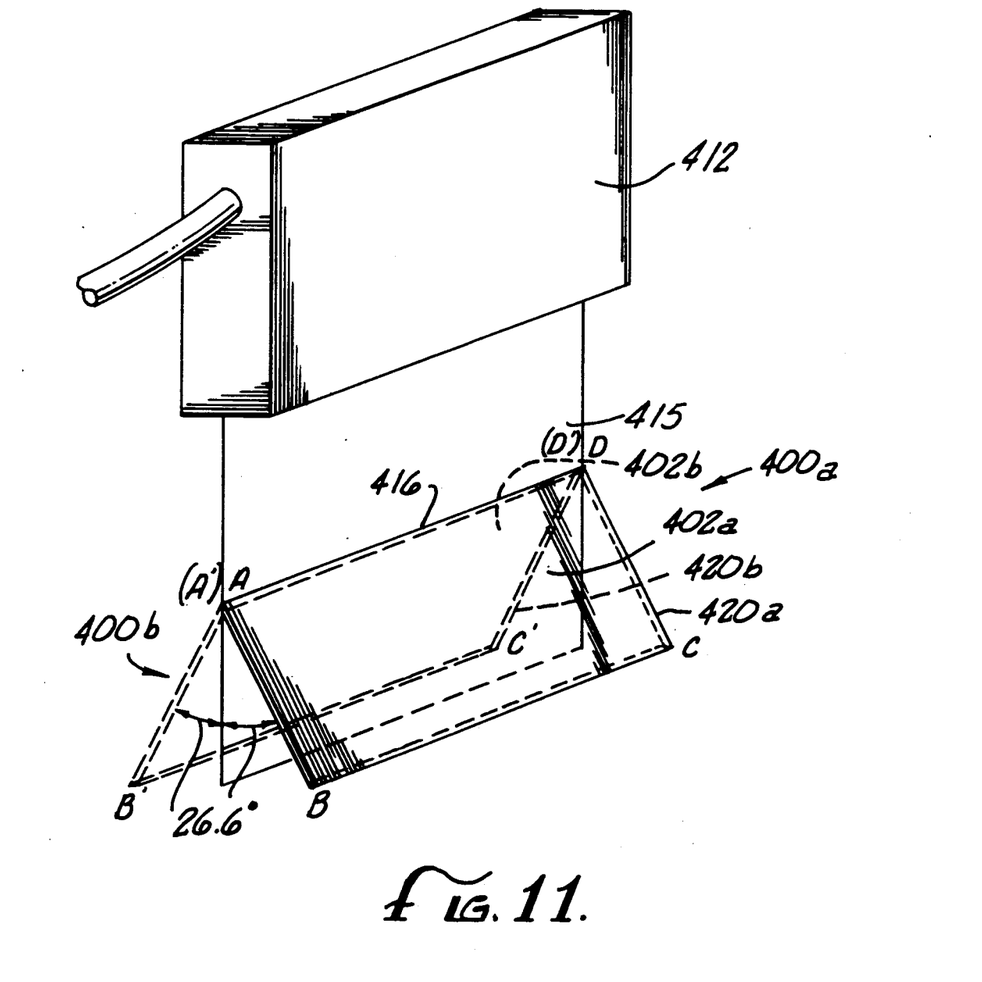
FIG. 11 is a perspective view of another alternative test object constructed in accordance with a still further aspect of the present invention.

FIG. 11 shows yet another alternative embodiment, similar in all respects to the embodiment in FIG. 10 except that the reflective surface (402a) is on the side of the plastic support structure (420a) opposite to that of the scanning plane (415) instead of adjacent to the scanning plane as in FIG. 10. The scanning plane (415) is aligned with the upper edge (416) of the reflective plane ABCD (400a) along line AD. Thus, the reflective plane (400a) comprises at least one target positioned in the scanning plane occupying a terminal position and a plurality of subsequent scanning targets positioned adjacent the scanning plane, down-range from the terminal target(s). As in FIG. 10, the reflective plane (400a) can be tilted to the opposite side (400b) as long as the scanning plane coincides with the upper edge (416) of the reflective plane A'B'C'D' along line A'D', wherein the terminal target(s) is(are) positioned. The angle of tilt of the reflective plane ABCD (400a) is 26.6 degrees with respect to the scanning plane (415), and the reflective surface (402a) is on the side of the plastic support structure (420a) opposite to that of the scanning plane.

It should be understood that the above described embodiment is simply illustrative of the principles of this invention and numerous other embodiments may be readily devised by those skilled in the art without deviating therefrom. Therefore only the following claims are intended to define this invention.

What is claimed:

1. A test object for use in the testing and calibration of ultrasonic diagnostic equipment used in scanning a plane of tissue by emitting an ultrasonic beam comprising at least one scanning target positioned in the scanning plane occupying a terminal position and a plurality of subsequent scanning targets positioned adjacent the scanning plane to reflect at least some of the ultrasonic beam for determining the width of the ultrasonic beam in a direction substantially normal to the plane.

2. The test object of claim 1 wherein said scanning targets are formed from a sheet of echogenic material.

3. The test object of claim 1 wherein said scanning targets are formed from a plurality of echogenic particles mounted in a substrate.

4. The test object of claim 1 wherein said scanning targets are positioned to form a wedge whose sides diverge from the scanning plane.

5. The test object of claim 1 wherein said scanning targets are positioned to form a wedge whose vertex is aligned with the scanning plane and comprises the terminal scanning target, and whose sides extend up-range from said terminal target.

6. The test object of claim 5 wherein the sides of the scanning target wedge diverge from the scanning plane at an angle of 26.6°.

7. The test object of claim 1 wherein said scanning targets are positioned to form a plane having an edge aligned with the scanning plane and comprising the terminal scanning target.

8. The test object of claim 7 wherein the sides of the scanning target plane extend up-range from said terminal scanning target.

9. The test object of claim 7 wherein the sides of the scanning target plane extend down-range from said terminal scanning target.

10. The test object of claims 8 or 9 wherein the sides of said scanning target plane diverge from the scanning plane at an angle of 26.6°.

11. A test object for use in the testing and calibration of ultrasonic diagnostic equipment used in scanning a plane of tissue by emitting an ultrasonic beam comprising a wedge-shaped array of targets having a vertex positioned in the scanning plane and sides up-range from said vertex at an angle of 26.6° with respect to the scanning plane.

12. A test object for use in the testing and calibration of ultrasonic diagnostic equipment used in scanning a planar of tissue by emitting an ultrasonic beam comprising a planar array of targets having an edge positioned in the scanning plane and extending from said scanning plane at an angle of 26.6° with respect to the scanning plane.

* * * * *